United States Patent
Kaufmann et al.

(10) Patent No.: US 8,876,886 B2
(45) Date of Patent: Nov. 4, 2014

(54) BRAIDED STENT TO BE IMPLANTED IN A BLOOD VESSEL

(75) Inventors: Ralf Kaufmann, Rangendingen (DE); Thomas Bogenschuetz, Hechingen-Stein (DE)

(73) Assignee: Jotec GmbH, Hechingen (DE)

( * ) Notice: Subject to any disclaimer, the term of this patent is extended or adjusted under 35 U.S.C. 154(b) by 0 days.

(21) Appl. No.: 12/434,507

(22) Filed: May 1, 2009

(65) Prior Publication Data

US 2009/0216307 A1 Aug. 27, 2009

Related U.S. Application Data

(60) Division of application No. 11/341,125, filed on Jan. 27, 2006, now abandoned, which is a continuation of application No. PCT/EP2004/008172, filed on Jul. 22, 2004.

(30) Foreign Application Priority Data

Jul. 30, 2003 (DE) .................................. 103 35 649

(51) Int. Cl.
*A61F 2/06* (2013.01)
*A61F 11/00* (2006.01)
*A61F 2/90* (2013.01)
*A61F 2/82* (2013.01)

(52) U.S. Cl.
CPC ........... *A61F 2/90* (2013.01); *A61F 2250/0018* (2013.01); *A61F 2002/823* (2013.01); *A61F 2250/0039* (2013.01)
USPC ......... 623/1.15; 606/108; 623/1.16; 623/1.32

(58) Field of Classification Search
CPC ............... A61F 2/82; A61F 2/06; A61F 2/07; A61F 2/91
USPC ........................ 623/1.11, 1.15, 1.13, 1.16, 1.3
See application file for complete search history.

(56) References Cited

U.S. PATENT DOCUMENTS

| 4,733,665 A * | 3/1988 | Palmaz .......................... 606/108 |
| 5,741,333 A * | 4/1998 | Frid .................................. 623/1.2 |
| 5,938,697 A | 8/1999 | Killion et al. |
| 5,951,599 A * | 9/1999 | McCrory ....................... 606/108 |
| 6,106,548 A | 8/2000 | Roubin et al. |

(Continued)

FOREIGN PATENT DOCUMENTS

| DE | 197 54 747 | 6/1999 |
| DE | 197 50 971 | 7/1999 |

(Continued)

OTHER PUBLICATIONS

International Search Report for PCT/EP2004/008172, mailed on Dec. 8, 2004, 5 pages.

*Primary Examiner* — Jason-Dennis Stewart
(74) *Attorney, Agent, or Firm* — Morrison & Foerster LLP

(57) ABSTRACT

A braided stent to be implanted in a blood vessel comprises a hollow body which is stretchable in its longitudinal direction and whose circumferential surface is formed by a braid of a multiplicity of filamentary elements which, in the expanded state of the braided stent, intersect a plane, perpendicular to the longitudinal direction, at a braiding angle. The braided stent has a smaller braiding angle in a central portion than in its distal and proximal portions which adjoin the central portion in the longitudinal direction.

11 Claims, 5 Drawing Sheets

(56) References Cited

U.S. PATENT DOCUMENTS

| | | | |
|---|---|---|---|
| 6,217,609 B1* | 4/2001 | Haverkost | 623/1.22 |
| 6,283,992 B1* | 9/2001 | Hankh et al. | 623/1.2 |
| 6,398,807 B1* | 6/2002 | Chouinard et al. | 623/1.35 |
| 7,029,494 B2* | 4/2006 | Soun et al. | 623/1.15 |
| 7,118,600 B2* | 10/2006 | Dua et al. | 623/23.68 |
| 7,226,473 B2* | 6/2007 | Brar et al. | 623/1.11 |
| 2001/0010013 A1* | 7/2001 | Cox et al. | 623/1.15 |
| 2003/0100945 A1 | 5/2003 | Yodfat et al. | |
| 2003/0130611 A1 | 7/2003 | Martin | |
| 2003/0135255 A1 | 7/2003 | Sundar | |
| 2003/0144725 A1* | 7/2003 | Lombardi | 623/1.13 |
| 2003/0153973 A1* | 8/2003 | Soun et al. | 623/1.16 |
| 2005/0283225 A1* | 12/2005 | Klisch | 623/1.15 |
| 2006/0070516 A1* | 4/2006 | McCullagh et al. | 87/9 |

FOREIGN PATENT DOCUMENTS

| | | |
|---|---|---|
| DE | 299 07 827 | 9/1999 |
| EP | 1 101 456 | 5/2001 |
| WO | WO-99/25271 | 5/1999 |
| WO | WO-02/071975 | 9/2002 |
| WO | WO-02/078570 | 10/2002 |

* cited by examiner

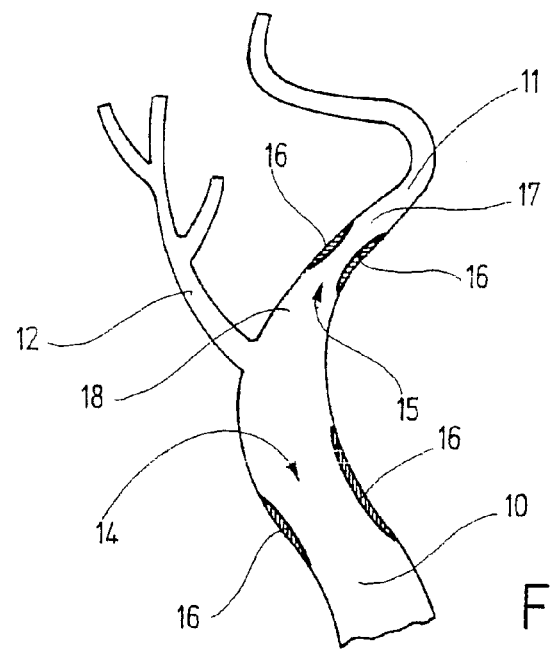
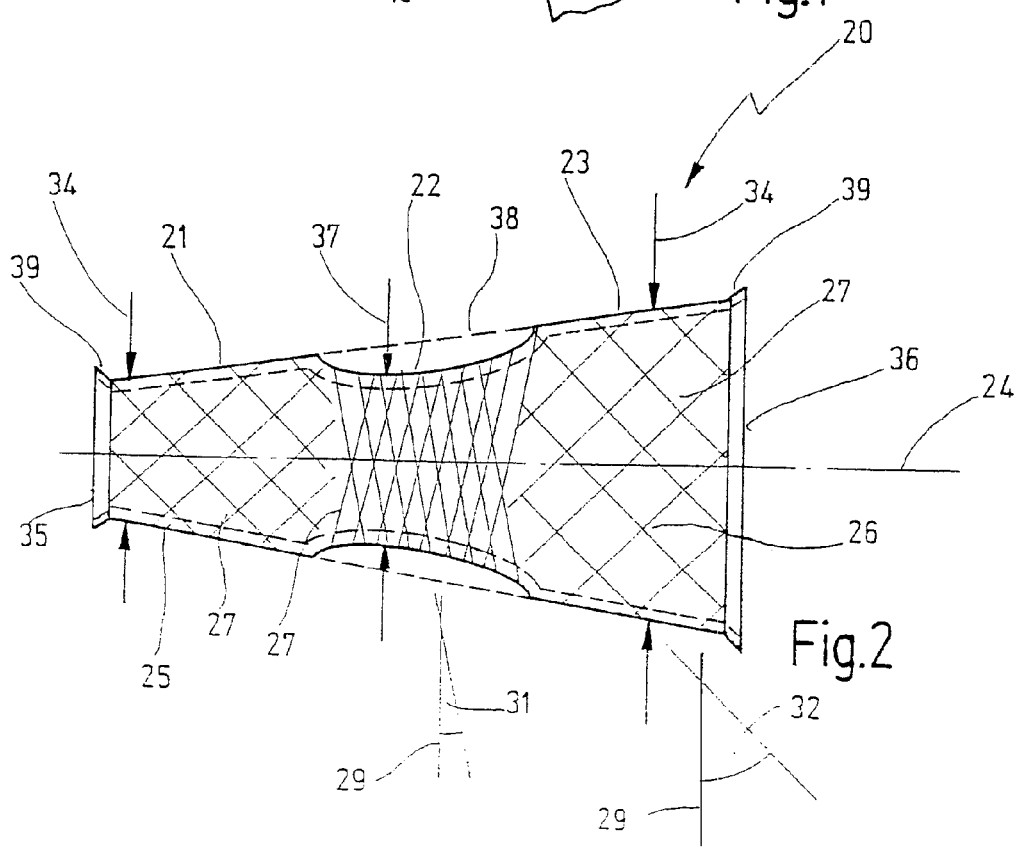

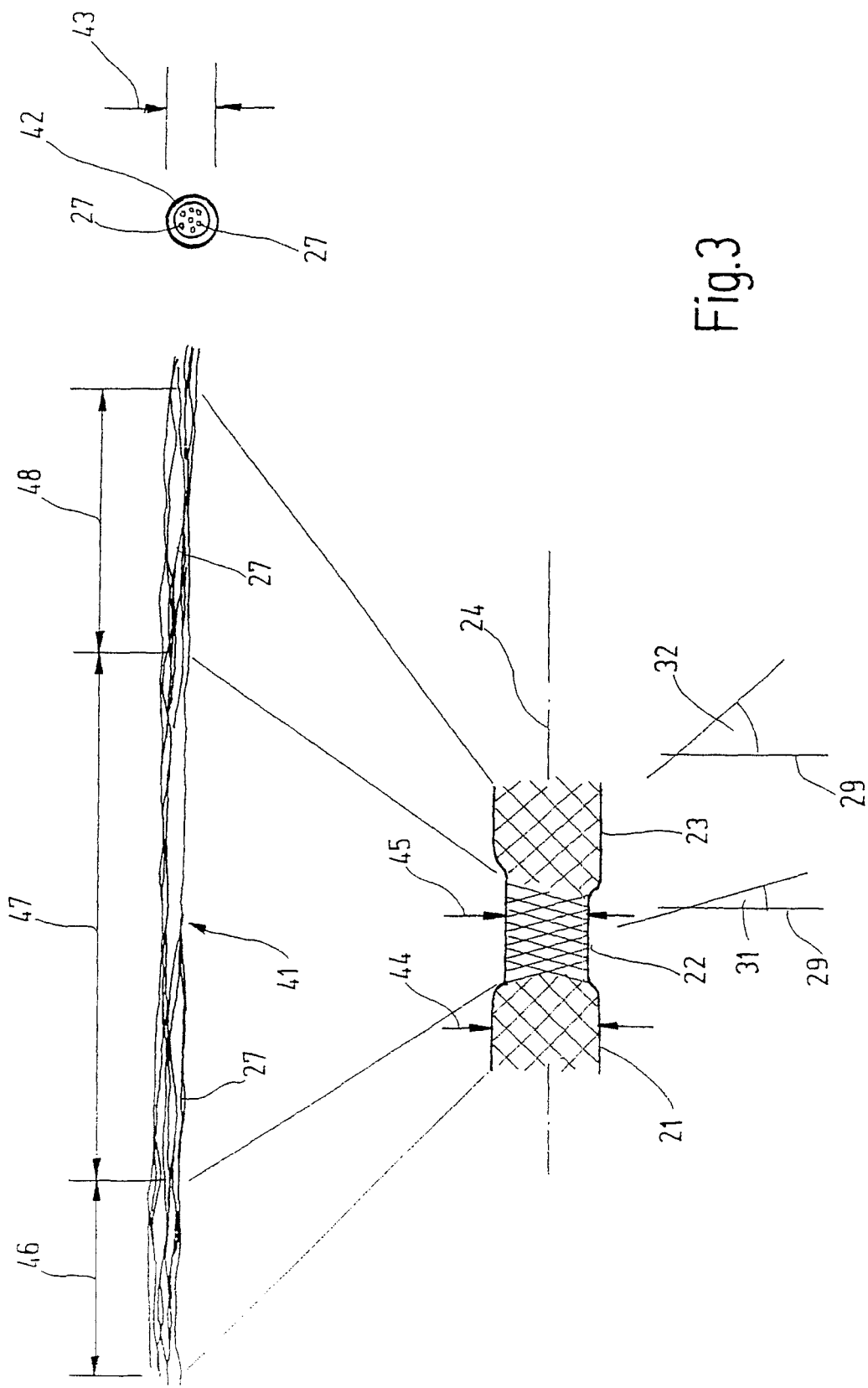

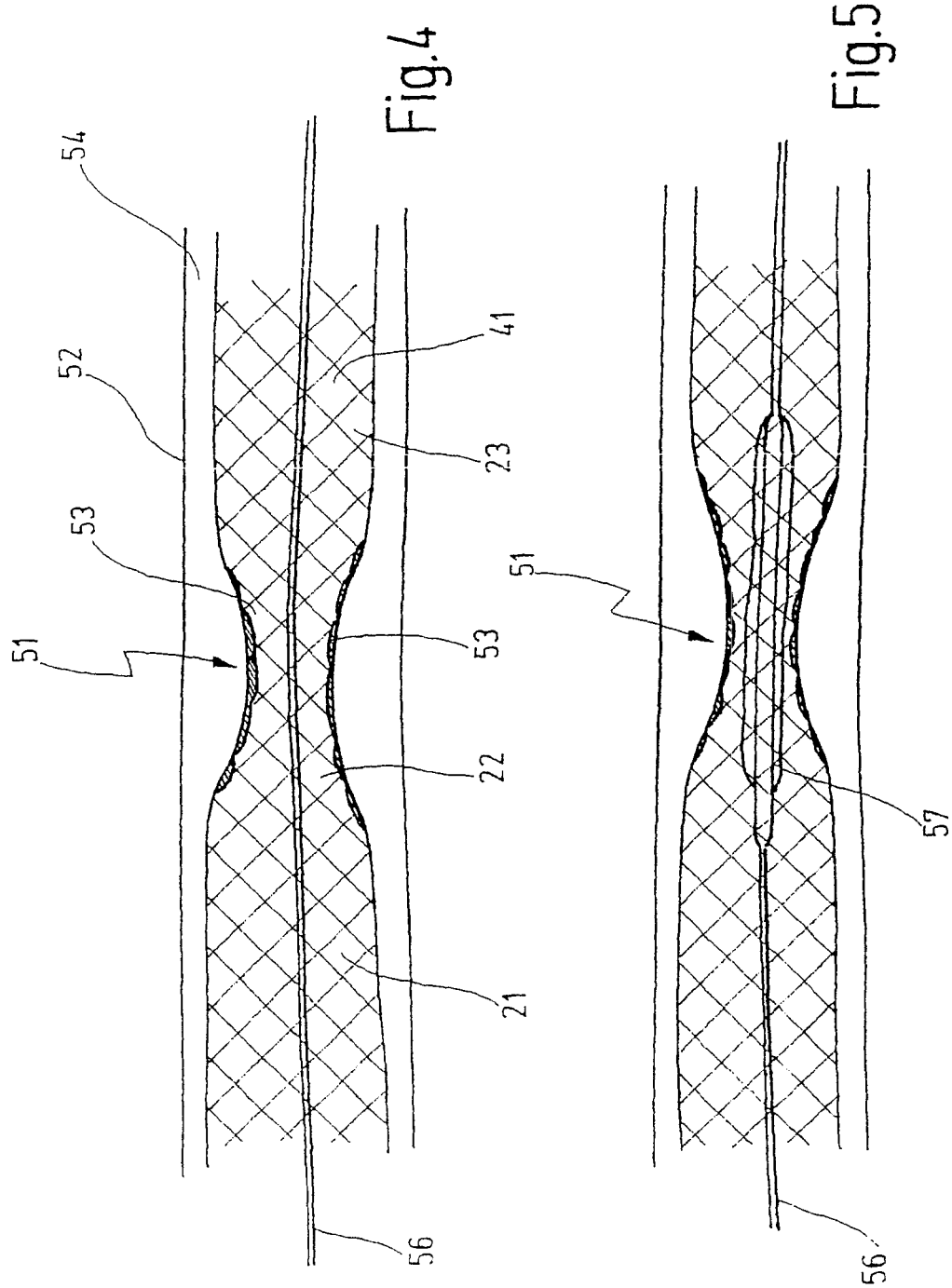

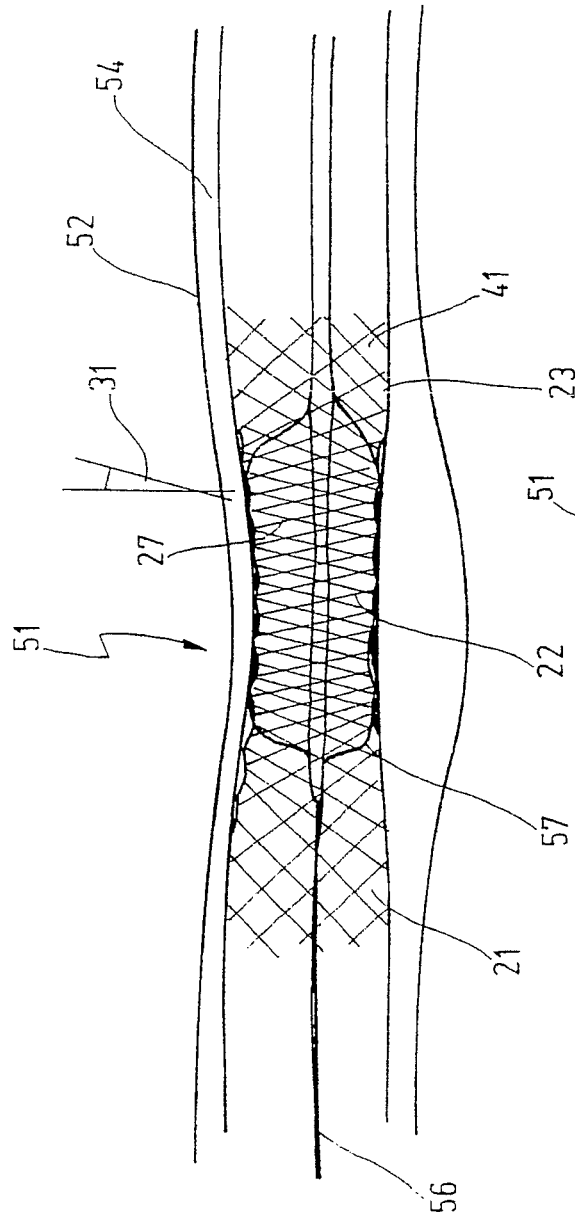
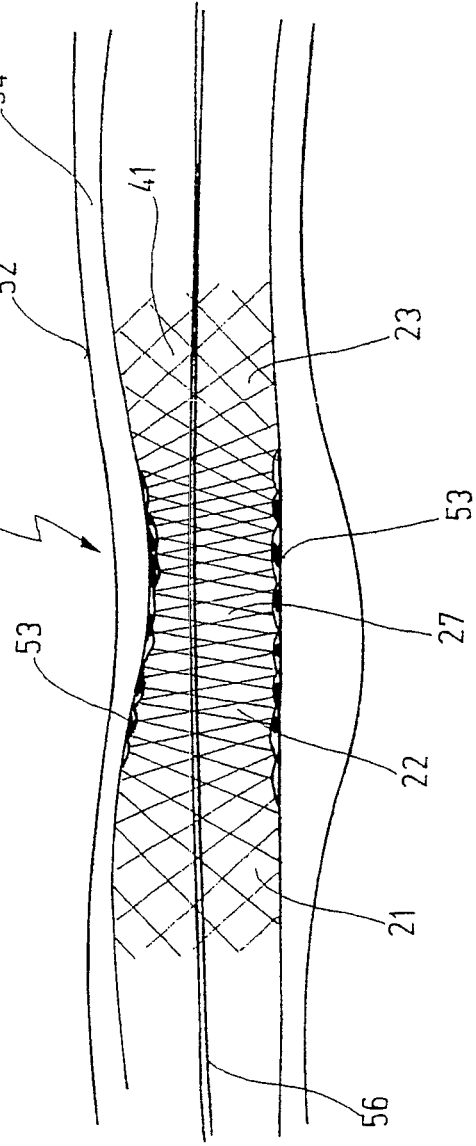

BRAIDED STENT TO BE IMPLANTED IN A BLOOD VESSEL

CROSS-REFERENCE TO RELATED APPLICATIONS

This is a divisional application of U.S. patent application Ser. No. 11/341,125, filed Jan. 27, 2006, which is a continuation application of International Patent Application PCT/EP/2004/008172, filed Jul. 22, 2004, designating the United States and published in German as WO 2005/011527 A1, which claims priority to German application number 103 35 649.5, filed Jul. 30, 2003. The contents of these documents are incorporated herein by reference.

TECHNICAL FIELD

The present invention relates to a braided stent to be implanted in a blood vessel, in particular in the carotid artery, with a hollow body which is stretchable in its longitudinal direction and whose circumferential surface has a braid comprising a multiplicity of filamentary elements which, in the expanded state of the braided stent, intersect a plane, perpendicular to the longitudinal direction, at a braiding angle.

BACKGROUND ART

A braided stent of this kind is known from the document DE 197 50 971 A1.

A stent is understood as a radially expandable endoprosthesis representing a typical intravascular implant which is implanted by a transluminal route and which is enlarged radially or expanded after it has been introduced percutaneously. Stents are used to strengthen blood vessels and to prevent restenosis in the vascular system following a previous angioplasty. They can be self-expanding or are expanded by a radial force applied from inside, for example if they are fitted on a balloon.

The stent known from DE 197 50 971 A1 has a hollow cylindrical body whose external diameter corresponds approximately to the internal diameter of the blood vessel in which the stent is to be implanted. The body of the stent is thus open in the longitudinal direction for the passage of blood. The circumferential surface is made up of a number of mutually offset filamentary elements which are braided together to form a braid with a multiplicity of polygonal cells. The braid can be constructed such that two intersecting systems of the filamentary elements are interlaced so that each filamentary element of one system is alternately guided over and under each filamentary element of the other system. Such a pattern of the braid is referred to as a plain weave.

The known stent can be stretched in its longitudinal direction on an applicator, by which means the diameter of the stent can be reduced for the purpose of implantation. The stent is introduced in the stretched or tensioned state into the vessel with the aid of the applicator. After the stent is positioned at the desired location in the vessel, the applicator is removed. Since no longitudinal extension forces now act on the stent, it relaxes elastically into its original length on account of its cell-like structure, expands radially outward and bears snugly on the inside wall of the vessel. This action can be intensified by using materials with a shape memory or by using a balloon catheter to assist or effect the expansion.

While it is known to produce braided stents of this kind continuously in the manner of yardage material, the braided stent known from DE 197 50 971 A1 is in each case produced individually, for which purpose the filamentary elements are reversed at each end of the stent during the braiding procedure. In this way, it is possible to give one end of the stent a crown which widens in a trumpet shape and by which an additional and particularly effective anchoring of the known stent in the blood vessel is achieved.

A disadvantage of braided stents of this kind is generally that they experience a considerable change in length upon stretching, the change in length being all the more pronounced the greater the original diameter and the smaller the original braiding angle. The correspondingly reversed reduction in length upon expansion of the braided stent is, however, often seen as a disadvantage. The positioning of a stent at the desired location in the blood vessel is of course a critical factor that decisively determines the action of the stent and the success of the medical intervention. Since the blood vessel area in which the stent is to be expanded is usually difficult for the practitioner to access, it is important that the diameter and the length of the stent in the expanded state are known exactly, so that it can be positioned with precision.

A further problem associated with braided stents is that the radial force and stiffness decline considerably even upon slight elongation of the stent, with the result that the exact dimensioning and positioning of a braided stent is more critical than in stents which do not shorten upon expansion. Such a stent is described for example in U.S. Pat. No. 6,106,548.

Braided stents are therefore not presently used in cases where a substantial radial force is to be exerted in a very precisely defined area of a blood vessel for the purpose of counteracting a restenosis.

A relatively new field of application for stents is the percutaneous treatment of lesions of the carotid artery following percutaneous angioplasty. The stenoses in the external carotid artery that are treated in this way are caused by arteriosclerosis of the vessel wall. This leads to a hard, brittle inner layer which constricts the blood stream more and more and thereby reduces the supply of blood to the brain. If an occlusion occurs, this results in a far-reaching stroke of the affected half of the brain and irreversible brain damage or even death.

The main complication of percutaneous angioplasty with subsequent stent implantation is caused, however, by the detachment of particles of the brittle inner layer, so-called plaque, which are entrained as emboli into regions of the brain, where they may trigger a local stroke with sometimes severe and irreversible brain damage.

Therefore, if the state of the vessel so permits, a "predilation" of the vessel by a balloon catheter is nowadays dispensed with, and instead a self-expanding stent is inserted directly by a percutaneous and transluminal route into the area of the stenosis. A particularly critical aspect of this, however, is the expansion phase of the stents. After their insertion and release within the stenosis, these stents in many cases do not develop a sufficient radial force to attain the shape in which they were manufactured. Therefore, after the stent has been put in place, a transluminal angioplasty balloon is introduced into the semi-deployed stent and inflated in order to widen the stent and the stenosis. This can lead to the aforementioned iatrogenic detachment of plaque material which, after deflation of the balloon, is entrained in the form of emboli into the brain.

To prevent the occurrence of strokes, so-called cerebral protection systems are therefore used with which the first emboli are trapped and removed. One such system is the PercuSurge system from PercuSurge Inc., Sunnyvale, Calif., USA. However, these cerebral protection systems entail a further intervention, often with clinical and symptom-related implications for the patients. Moreover, however, particles of plaque that have already loosened may also become detached several days after the stent implantation and may pass through the meshes of a conventional stent into the blood stream and thus trigger serious strokes.

To solve this problem, EP 1 101 456 A1 proposes a stent which, in its central portion, is ensheathed with a biocompatible, elastic material and comes to lie between the endoprosthesis and the wall of the blood vessel after implantation of the stent. In this way, the thrombogenic material is held on the wall, thus preventing plaque from detaching and passing into the blood stream.

However, this "ensheathed" stent has a whole series of disadvantages, in particular for the proposed application. First, the elastic membrane surrounding it prevents anchoring of the stent in the wall of the blood vessel, with the result that there is a risk of its changing position and losing its protective effect. Moreover, the known stent is expensive and complicated to produce, which fact is attributable to the additionally required elastic membrane.

The aforementioned U.S. Pat. No. 6,106,548 is also concerned with the problem of detachment of plaque and its transport as emboli into the brain.

The known stent comprises a large number of rings which each include V-shaped struts. Adjacent rings are interconnected by wave-shaped connecting members which are in each case secured at the apices of V-shaped struts in adjacent rings. These connecting members compensate for the change in length of the rings during expansion, with the result that the stent does not change its length when it is expanded in the blood vessel. Said document further states that the external diameter of the known stent should be slightly greater than the internal diameter of the blood vessel in order to anchor the stent securely at the desired position and prevent it from moving out of its position.

The meshes formed by the V-shaped struts and connecting members can have different mesh widths in different sections, with smaller meshes being used to prevent detachment of plaque.

The known stent can be configured such that, in the expanded state, it has areas with different external diameters, such that it can adapt to vessels or bifurcations where the lumen diameters vary, as is the case for example at the carotid bifurcation.

The known stent is produced from a small tube using a laser cutting technique or is made from prefabricated V-shaped struts and connecting members which are subsequently connected to one another, for example by welding.

Given the demand that this stent should not shorten during expansion, it can be manufactured only by technically complex means, with the result that its production is very cost-intensive.

A stent which likewise shortens only slightly during expansion is known from U.S. Pat. No. 5,938,697. This document is concerned with the problem that, although stents with an equal radial force along their length are able to keep a blood vessel open in the stenosed area, their outer portions press more strongly than is needed against healthy areas of the vessel. Comparable problems are seen in conical areas of vessels, for example at the carotid bifurcation.

The known stent solves this problem by exerting radial forces that vary along its longitudinal extent and by having a differing stiffness.

For this purpose, the stent is made up of annular sections of serpentine-like segments which extend in a zigzag shape around said section. The individual rings are interconnected by means of all or some of the adjacent zigzag segments being connected to one another by struts at their apices. By virtue of the dimensions of these struts and the number of the struts between two rings, a more open or more closed structure is achieved because less or more metal is present between the rings. The rings themselves are identical. This configuration is intended to ensure that the ratio of metal surface to blood vessel surface is constant along the length of the stent.

The stent has the so-called closed structure in those areas in which good stiffness and plaque coverage are to be achieved, whereas the so-called open structure is to be found in areas where greater flexibility is to be achieved.

In one illustrative embodiment, the stent has a central portion in which it exerts a very high radial force, whereas the radial force in the adjoining distal and proximal portions is much less.

A disadvantage of this stent is that it does not provide any effective protection against detachment of plaque, and, in addition, even the excessively high pressure on the vessel wall in the stenosed area cannot prevent extremely small particles of plaque from detaching and passing into the blood stream through the meshes in the individual rings.

DISCLOSURE OF THE INVENTION

In view of the above, an object of the present invention is to make available a stent which, on the one hand, anchors securely in the stenosed area, and, on the other hand, effectively prevents detachment of plaque and the latter's entry into the blood stream as emboli.

In the braided stent mentioned at the outset, this object is achieved, according to the invention, by the fact that it has a smaller braiding angle in a central portion than in its distal and proximal portions which adjoin the central portion in the longitudinal direction.

This object underlying the invention is achieved completely by this means.

The inventors of the present application have in fact found that the object on which the invention is based can actually be achieved using a braided stent if its disadvantages in relation to other stent structures are deliberately exploited. By means of the small braiding angle, the braided stent according to the invention can be stretched considerably in the central portion, which is actually unwanted, but, for this very reason, in its expanded state, it has a substantial density in the central portion and is also particularly stiff there, in other words can take up forces from outside. By virtue of its substantial density and stiffness in its central portion, the novel braided stent affords good protection against detachment of plaque and, with its narrow meshes in this portion, it also ensures that any plaque that has nevertheless become detached cannot pass into the blood stream.

Independently of its shape and the local braiding angles, the novel braided stent can also be loaded into an elongate catheter which at least has a luminal cross-sectional surface area corresponding to the sum of all the braided wire cross sections.

According to another object of the invention, the central portion, in the expanded state, has a smaller external diameter than the distal and the proximal portions.

The advantage of this measure is that the diameter in the central portion is chosen such that the braid meshes open out completely there and can reduce their angle in the direction of the predetermined braiding angle, in which process the braided stent as a whole shortens considerably. Because of the slightly smaller diameter, the extreme shortening during expansion is also reduced in the central portion. By means of the slightly smaller diameter, the pressure on the stenosis is also reduced and the braided stent remains leaktight. On the other hand, the compact central portion reacts almost like a thin-walled tube section with closed jacket when an outer compression occurs. The distal and proximal portions brace themselves with their wire ends in the vessel walls. Because of their greater external diameter, the distal and the proximal portions therefore exert a much greater radial force on the inside wall of the vessel than does the central portion. The invention therefore takes exactly the opposite approach from that proposed in U.S. Pat. No. 5,938,697 discussed above.

The invention also departs from the concept proposed in U.S. Pat. No. 6,106,548 discussed above, in accordance with which a stent to be fitted in the area of the carotid bifurcation is not allowed to shorten during expansion.

The inventors have found that the novel braided stent braces itself at its distal and proximal portions in such a way as to prevent a possible lengthening and thus a reversal of the small braiding angle in the central portion. In this way, a high degree of stiffness is maintained in the area of the stenosis, and, at the same time, a very dense braid is created which prevents the escape of emboli. Ideally, the internal diameter of the stent in the area of the central zone corresponds to the maximum diameter of the PTA balloon (percutaneous transluminal angioplasty balloon) and thus to the intended widening of the stenosis. This choice of the diameters prevents a situation where, in the central portion, an incompletely expanded stent zone arises which would have insufficiently fine meshes and insufficient protective action. On account of the greater braiding angle and diameter in the distal and proximal portions, the wire ends there open out better against the vessel walls lying distally and proximally of the stenosis and the stent shapes itself more gently thereon.

According to a further object of the invention, the braided stent, in its expanded state, has an external diameter which changes continuously, preferably decreases, from its proximal end to its distal end, and it is further preferred if the external diameter in the central portion is reduced still further compared to a continuous change.

In this way, a conical stent is created which has a greater density in the central portion than in the two outer portions. In this way, the stent is particularly well suited for use in the internal carotid artery.

If the external diameter in the central portion is smaller than is defined by the cone shape, this means that, in a conical stent too, it is possible to obtain the advantages already discussed above and associated with the reduced diameter in the central portion.

According to a still further object, at the distal and proximal portions, the braided stent has an external diameter which is greater than the internal diameter of the blood vessel at the site where the respective portion lies after the implantation.

The advantage of this measure is that the braided stent braces itself very firmly in the inside wall of the vessel in the areas distal and proximal of the stenosis, so that the position of the central portion is fixed. For this reason, it is not absolutely necessary that the central portion fixes itself in its position, as this is already effected by the two outer portions. As has already been mentioned, this fixing of the central portion has the effect that the small braiding angle and thus the leaktightness in the central portion are maintained.

According to a further object, in the central portion, the braided stent has an external diameter which is equal to or slightly smaller than the dilated internal diameter of the blood vessel at the site where the central portion lies after the implantation.

This measure has the advantage that the central portion can expand completely so that the filamentary elements are able to assume the predetermined braiding angle again, that is to say they open out and ensure a substantial leaktightness and a corresponding stiffness in the central portion.

In one embodiment of the above-mentioned measures, the braid has a plaine weave.

In this type of braid, the intersecting helical yarns of filament cross one another in such a way that each filamentary element of the one system is alternately guided over and under each filamentary element of the other system. The resulting polygonal meshes are diamond-shaped in this braid pattern. This kind of braid has proven particularly suitable for stents intended for implantation in blood vessels.

In another embodiment, the filamentary elements are made from a material with a shape-memory effect, in particular from nitinol.

The advantage of this measure is that the novel braided stent, because of its superelasticity, automatically resumes its original shape after release at the stenosed site; the widening, in particular in the area of the stenosis, can also be assisted, however, by a balloon catheter in order to ensure that the meshes in the central portion right themselves completely.

In one embodiment, the braided stent is coated with a medically active substance.

This measure is known per se, and the medically active substances can, for example, prevent restenosis, accelerate healing of wounds of the inside wall of the vessel, or prevent the development of inflammations.

In a further embodiment, the braided stent has a conically widening crown shape at its two ends.

The advantage of this measure is that the novel braided stent is anchored still more effectively at its two ends in the inside wall of the vessel. As a result of the expansion of the released braided stent, which expansion may be assisted by a balloon catheter, the braided stent shortens considerably, especially because of the small braiding angle in the central portion, with the result that the outer ends move toward the central portion. On account of the pressure acting from outside on the braided stent, the latter tends to lengthen again after deflation of the balloon, which lengthening is prevented by the widened crowns. The crowns can be used as an additional or alternative measure for increasing the external diameter at the distal and proximal portions beyond the internal diameter of the blood vessel.

Another object of the invention is a method for treating an aneurysm comprising the step of implanting the stent according to the invention into a vessel comprising an aneurysm at the position of the aneurysm.

An aneurysm is understood as a dilation or protuberance of an arterial blood vessel resulting from congenital or acquired lesions of the vessel wall. The protuberance can involve the whole of the vessel wall or, in the case of a so-called false aneurysm, blood from the vessel lumen can escape between the tissue wall layers and tear these apart. Nontreatment of an aneurysm can lead, in advanced stages, to a rupture of the blood vessel, whereupon the patient may suffer massive and fatal internal bleeding.

Aneurysms often occur in the area of the abdominal aorta or internal thoracic artery, but also in the areas of the ascending or descending branch of the aorta, and in the arteries of the brain.

The inventors have found that the stent can be braided to extremely small diameters, as a result of which it can be used for applications in very small vessels too, for example in the arteries of the brain.

When used in an aneurysm of a peripheral vessel, for example in arteries of the brain, the central portion can be positioned in such a way that this portion can form a compact structure without radially acting wall pressures. Since the central portion has a smaller braiding angle than the distal and proximal portions which adjoin it in the longitudinal direction of the stent, a dense zone forms in the area of the central portion, through which dense zone no blood or only a little blood passes into the area of the aneurysm. By means of the proximal and distal portions of the stent, the latter is firmly anchored in those areas of the vessel which are not affected by the aneurysm, with the result that all blood is guided into the braided stent and leaves the latter again at the distal end past the aneurysm. Accordingly, the more permeable end areas of the stent are used on the one hand for fixing it axially in healthy vessel areas and on the other hand permit blood circulation in branching-off vessels at the margin of the aneurysm. By means of the central portion which, on account of its small braiding angle, forms a compact zone, the blood in the aneurysm is virtually prevented from exchange with the circulating blood. In this way, clots are able to form in the aneurysm, as a result of which the latter's further growth is stopped. The central compact portion at the same time ensures that the clots formed in the area of the aneurysm cannot pass into the blood stream. At the same time, however, the circulation in the main vessel and in branching-off vessels is not impaired.

Further advantages will become evident from the description and from the attached drawing.

It will be understood that the aforementioned features and those still to be explained below can be used not only in the respectively given combination, but also in other combinations or on their own, without departing from the scope of the present invention.

BRIEF DESCRIPTION OF THE DRAWINGS

Embodiments of the invention are shown in the drawing and are explained in more detail in the following description. In the drawing:

FIG. 1 shows the geometric situation at the left carotid bifurcation in humans;

FIG. 2 shows a conical braided stent for implantation in the internal carotid artery from FIG. 1;

FIG. 3 shows a cylindrical braided stent for implantation in the common carotid artery from FIG. 1;

FIG. 4 shows a blood vessel with stenosis and inserted braided stent from FIG. 3;

FIG. 5 shows the blood vessel from FIG. 4 with inserted PTA balloon;

FIG. 6 shows the blood vessel from FIG. 5 with expanded PTA balloon;

FIG. 7 shows the blood vessel from FIG. 6 with the PTA balloon re-moved and a completely expanded braided stent.

MODES OF CARRYING OUT THE INVENTION

Description of Preferred Embodiments

Figure 8:
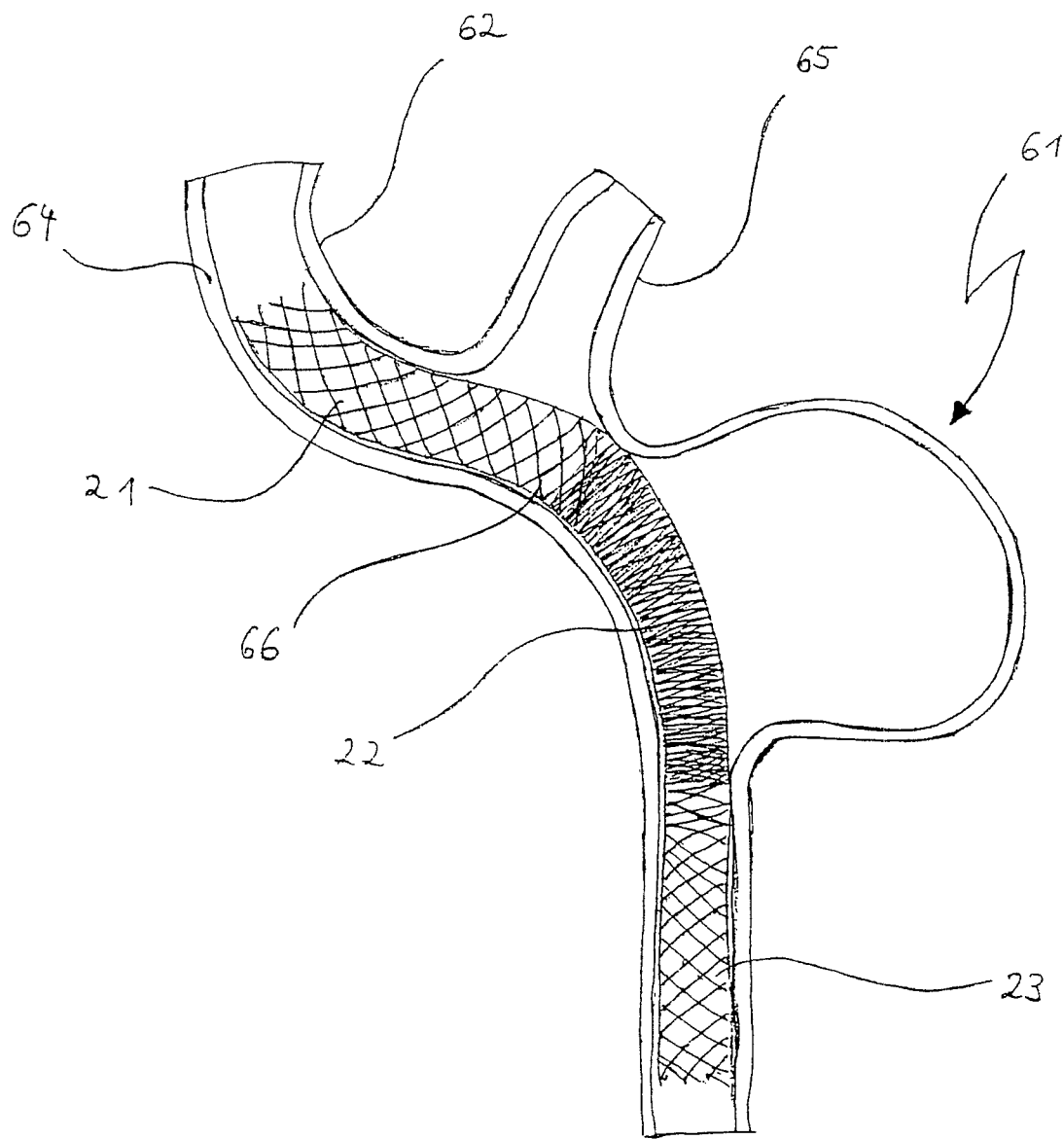
FIG. 8 shows a blood vessel with aneurysm and inserted braided stent from FIG. 3.

FIG. 1 shows the geometric situation at the carotid bifurcation in a human. The common carotid artery 10 merges here into the internal carotid artery 11, with the external carotid artery 12 branching off. A stenosis 14 in the common carotid artery and a stenosis 15 in the internal carotid artery 11 are indicated by hard, brittle areas 16. It will be noted that the internal carotid artery 11 has a smaller internal diameter in an area 17 in the distal direction from the stenosis 15 than it does in an area 18 in the proximal direction from the stenosis 15.

FIG. 2 shows a braided stent 20 according to the invention which is intended to be inserted into the area of the stenosis 15 in FIG. 1. The braided stent 20 has a distal portion 21, a central portion 22 and a proximal portion 23 arranged one after the other in the longitudinal direction 24 of the braided stent 20.

The braided stent 20 has a hollow body whose circumferential surface indicated by 25 is made from a braid 26 of filamentary elements 27 which, in the present case, are of nitinol wire. The braid 26 is in the form of a plain weave, as is described in the aforementioned DE 197 50 971 A1, which is incorporated by reference herein.

In FIG. 2, the braided stent 20 is shown in its completely expanded state, that is to say in the finished state, in which the filamentary elements 27 in the central portion 22 intersect a plane 29, perpendicular to the longitudinal direction 24, at a braiding angle 31 which is considerably smaller than the braiding angle 32 in the distal and proximal portions 21 and 23, respectively.

The braided stent 20 has an external diameter 34 which continuously decreases from its proximal end 36 to its distal end 35, so that it generally has a conical structure corresponding to the conical shape of the internal carotid artery 11 in the area of the stenosis 15 from FIG. 1.

In the central portion 22, the external diameter 37 is reduced compared to the cone shape indicated by the broken lines at 38. It is with this central portion 22 of reduced external diameter 37 that the braided stent 20 from FIG. 2 comes to lie in the area of the brittle areas 16 of the stenosis 15, the distal portion 21 coming to lie in the distal area 17 of the internal carotid artery.

By means of the small braiding angle 31 in the central portion 22, the braided stent 20 there has a very dense mesh structure which presses the areas 16 against the inner wall of the internal carotid artery 11 and prevents them from detaching and passing into the blood stream.

In the area of the distal portion 21 and proximal portion 23, the external diameter 34 of the braided stent 20 is greater than the corresponding internal diameter of the internal carotid artery 11, whereas the external diameter 37 is approximately equal to the internal diameter of the internal carotid artery 11 in the area of the stenosis 15 after suitable dilation.

In this way, the braided stent 20 is braced with its distal and proximal portions 21 and 23, respectively, in the internal carotid artery and prevents the central portion 22 from lengthening, which would lead to an increase in the braiding angle 31. However, the braided stent 20 in the central portion 22 is held with its braid meshes at the braiding angle 31 such that the central portion 22 not only has a very dense structure but, in addition, a suitable stiffness which prevents further contraction in the area of the stenosis 15.

FIG. 3 shows a braided stent 41 which is intended to be inserted into the area of the stenosis 14 from FIG. 1. At the bottom of FIG. 3, the braided stent 41 is shown in the completely expanded state, and it will be seen from this that it has a hollow cylindrical shape. At the top of FIG. 3, the braided stent 41 is shown in its elongated form in which it is loaded into a catheter 42 indicated schematically on the right of FIG. 3, the internal diameter 43 of said catheter 42 being chosen such that it has a luminal cross-sectional surface area corresponding to the sum of the cross-sectional surface areas of the braided wires 27.

In its distal and proximal portions 21 and 23, respectively, the braided stent 41 has an external diameter 44 which is slightly greater than the internal diameter of the common carotid artery in the area of the stenosis 14. In its central portion 22, the braided stent 41 has a reduced external diameter 45 which corresponds approximately to the internal diameter of the braided stent in the areas 16 after suitable dilation.

Like the braided stent 20 above, the braided stent 41 also has, in the central portion 22, a braiding angle 31 which is smaller than the braiding angle 32 in the distal and proximal portions 21 and 23, respectively.

Due to the small braiding angle 31, the central portion 22 stretches considerably further than the distal and proximal portions 21 and 23. In the fully stretched state, as is shown at the top of FIG. 3, the length 46 of the distal portion 21 is about 30 to 60% greater than in the expanded state. The same applies to the length 48 of the proximal portion 23.

Because of the very much smaller braiding angle 31, the length 47 of the central portion 22 in the stretched state is about 500 to 600% of the length in the expanded state, as is shown at the bottom of FIG. 3.

FIG. 4 now shows a schematic side view of a stenosis 51 in a blood vessel 52 in which plaque 53 has gathered on the vessel wall 54, the vessel wall 54 being further constricted in the area of the stenosis 51. In FIG. 4, the braided stent 41 from FIG. 3 has already been introduced into the area of the stenosis 51 so that the central portion 22 lies in the area of the constriction and plaque 53, whereas the distal and proximal portions 21 and 23 lie distally and proximally of the stenosis 51. The braided stent 41 was introduced in the customary way using the catheter 42 shown in FIG. 3 and was then released, so that it was able to deploy into the shape shown in FIG. 4. Particularly if the filamentary elements 27 are made of nitinol wire, that is to say have a shape memory, the braided stent 41 expands into its original shape. However, the expansion force of the braided stent 41 is sometimes not enough to keep the braid meshes sufficiently open to ensure, especially in the central portion 22, that the braiding angle 31 is adopted.

For this purpose, a PTA balloon 57 is introduced with the aid of a guide wire 56 into the area of the stenosis 51, as is shown in FIG. 5.

The PTA balloon 57 is then inflated, as a result of which the constriction in the area of the stenosis 51 widens, as is shown in FIG. 6. Ideally, the PTA balloon is inflated until it has an external diameter corresponding to the internal diameter of the braided stent 41 in the area of the central portion 22 in its original form, i.e. when the filamentary elements 27 have again reached the braiding angle 31. The situation is shown in FIG. 6. The external diameter of the braided stent 41 in the central portion 22 is now approximately equal to the dilated internal diameter of the blood vessel 52 in the area of the stenosis 51. Comparing this to FIG. 5, it will be seen that the braided stent 41 has shortened considerably, especially in the portions 21 and 23, as a result of a kind of reduction in the manner of scissors.

After it has been deflated, the PTA balloon 57 is removed so that the situation shown in FIG. 7 arises in which the filamentary elements 27 in the central portion 22 of the braided stent 41 form a dense mesh network by which the plaques 53 are held firmly against the inside of the vessel wall 54, so that said plaques cannot pass into the blood stream.

Upon expansion of the braided stent 41 with the aid of the PTA balloon 57, the braided stent 41 shortens, its outer areas moving—so to say—towards the stenosis 51. By means of the pressure exerted by the vessel wall 54 on the braided stent 41, the latter is now anchored at the distal and proximal portions 21 and 23 on the inside of the vessel wall 54, so that, in the central portion 22, the braiding angle 31 is maintained and the required compactness of the braid and stiffness are thus guaranteed.

FIG. 8 shows a schematic side view of an aneurysm 61 in a blood vessel 62 and an accessory vessel 65. The vessel wall 64 of the vessel 62 is sheared apart in the area of the aneurysm 61. In FIG. 8, the braided stent 66 has been introduced in the area of the aneurysm 61 so that the central portion 22 lies in the area of the sheared-apart vessel walls 62 of the aneurysm 61, while the distal and proximal portions 21 and 23 lie distally and proximally of the aneurysm 61. As has already been described for FIG. 4, the braided stent 66 was introduced in the customary manner into the vessel and released so that it was able to deploy into the shape shown in FIG. 8.

It will be seen from FIG. 8 that the central area forms a dense zone through which the blood carried in the vessel cannot pass into the area of the aneurysm 61, and instead the blood is conveyed onward in the vessel via the proximal portion 23. At the same time, the distal portion 21, whose braid structure is less dense than that of the central portion 22, ensures that blood can escape from the braided stent in this area, as a result of which the contiguous vessel 65 remains supplied with blood and at the same time the stent 66 remains securely anchored in the vessel 62. By means of the central, dense portion 22, the blood in the aneurysm 61 is virtually prevented from exchange with the circulating blood, as a result of which a clot formation in the aneurysm 61 can be obtained. At the same time, the braided stent 66, as a result of its position in the vessel 62, ensures that clots formed in the aneurysm 61 cannot pass into the vessel 62 and possibly trigger emboli in adjoining vessels.

The invention claimed is:

1. A method of implanting a braided stent into a blood vessel having an aneurysm area, comprising:
   a): introducing a one-piece braided stent in a stretched state to a site of implantation having an aneurysm, wherein the one-piece braided stent in the stretched state is stretched along a longitudinal direction of the one-piece braided stent; and
   b): deploying the one-piece braided stent into an expanded state so that a proximal portion and a distal portion of the one-piece braided stent lie proximally and distally, respectively, from the aneurysm, and a central portion of the one-piece braided stent lies, at least partially, adjacent a stenosis of the aneurysm area,
   wherein the one-piece braided stent has multiple filaments that, in the expanded state, intersect a plane perpendicular to the longitudinal direction at a braiding angle, wherein the braiding angle is relative to a transverse direction of the stent, the braiding angle of the one-piece braided stent being smaller in the central portion than in the proximal and distal portion, wherein the smaller angle of the braided stent in the central portion forms a dense mesh network of the filaments, wherein the dense mesh network prevents transport of plaque from the aneurysm area, wherein the diameter of the stent in the central portion is approximately equal to or less than a dilated internal diameter of the stenosis when the stent is in an unrestrained state, and wherein a length of the central portion of the stent in the stretched state is 500-600% greater than a length of the central portion in the expanded state.

2. The method of claim 1, further comprising elongating the braided stent into the stretched state and loading the braided stent in its stretched state onto an applicator.

3. The method of claim 1, wherein, in the expanded state, the central portion has a smaller external diameter than the distal and the proximal portions.

4. The method of claim 1, wherein the deploying of the braided stent further comprises expanding an external diameter of the braided stent to a predetermined size.

5. The method as in claim 1, wherein the deploying of the braided stent further comprises expanding the diameter of said central portion using a percutaneous transluminal angioplasty (PTA) balloon.

6. The method of claim 1, wherein at least one of the proximal portion and the distal portion has a conically widened crown configured to anchor the stent against an inside wall of the blood vessel and reduce lengthening of the stent.

7. The method of claim 1, wherein the dense mesh network of filaments open completely when the stent is in the expanded state.

8. The method of claim 1, wherein the central portion does not exert pressure on the stenosis when the stent is in the expanded state.

9. The method of claim 1, wherein a length of the distal portion of the stent in the stretched state is 30-60% greater than a length of the distal portion in an expanded state.

10. A method for treating an aneurysm comprising:
   implanting a braided stent into a vessel having an aneurysm at a position adjacent a stenosis of the aneurysm, wherein the braided stent comprises a hollow cylindrical body which stretches in its longitudinal direction, the braided stent, in an expanded state, having an external diameter that continuously decreases from its proximal end to its distal end and a circumferential surface comprising a braid of a multiple filaments that, in the expanded state of the braided stent, intersect a plane, perpendicular to the longitudinal direction, at a braiding angle, wherein the braiding angle is relative to a transverse direction of the stent, wherein
   the braided stent has a smaller braiding angle in a central portion than in its distal and proximal portions which adjoin the central portion in the longitudinal direction, wherein the smaller angle of the braided stent in the central portion forms a dense mesh network of the filaments, wherein the dense mesh network prevents transport of plaque from the aneurysm, and wherein the diameter of the stent in the central portion is approximately equal to or less than a dilated internal diameter of the stenosis when the stent is in an unrestrained state, and wherein a length of the central portion of the stent in a stretched state is 500-600% greater than a length of the central portion in an expanded state.

11. A method of implanting a braided stent into a blood vessel having a stenosis area, comprising:
   a): introducing a one-piece braided stent in a stretched state into a blood vessel to a site of implantation having a stenosis, wherein the one-piece braided stent in the stretched state is stretched along a longitudinal direction of the one-piece braided stent; and
   b): deploying the one-piece braided stent into an expanded state so that a proximal portion and a distal portion of the one-piece braided stent lie proximally and distally, respectively, from the stenosis, and a central portion of the one-piece braided stent lies, at least partially, adjacent the stenosis area, wherein
   the one-piece braided stent has multiple filaments that, in the expanded state, intersect a plane perpendicular to the longitudinal direction at a braiding angle, wherein the braiding angle is relative to a transverse direction of the stent, the braiding angle of the one-piece braided stent being smaller in the central portion than in the proximal and distal portion, wherein the filaments in the central portion form a dense mesh network by which the plaques are held firmly against an inside wall of the blood vessel, wherein the diameter of the stent in the central portion is approximately equal to or less than a dilated internal diameter of the stenosis area when the stent is in an unrestrained state, and wherein a length of the central portion of the stent in the stretched state is 500-600% greater than a length of the central portion in the expanded state.

* * * * *